United States Patent [19]

Tolbert et al.

[11] 4,268,629

[45] May 19, 1981

[54] PRODUCTION OF ANGIOGENIC FACTOR BY CELL CULTURE

[75] Inventors: William R. Tolbert, Manchester; Mau-Jung Kuo, Chesterfield; Joseph Feder, University City, all of Mo.

[73] Assignee: Monsanto Company, St. Louis, Mo.

[21] Appl. No.: 126,811

[22] Filed: Mar. 3, 1980

[51] Int. Cl.[3] .............................................. C12P 1/00
[52] U.S. Cl. .................................... 435/41; 435/240; 435/948
[58] Field of Search .......................... 435/41, 240, 241

[56] References Cited

PUBLICATIONS

Adv. Canc. Res. 19, 331-358 (1974).
Arch. Dermatol, 111, 321-327 (1975).
J. Invest. Dermatol. 61, 130-141 (1973).
Microvas. Res. 10, 396-413 (1975).
Proc. Natl. Acad. Sci. USA 75, (2) 847-851 (1978).
Nichols, Science, vol. 196, pp. 60-63 (1977).

*Primary Examiner*—Alvin E. Tanenholtz
*Attorney, Agent, or Firm*—Scott J. Meyer; James W. Williams, Jr.

[57] ABSTRACT

Process for the production of human angiogenic factor in vitro comprising growing the human diploid cell line IMR-90 on support surface in nutrient culture medium at about 35°–38° C. for a sufficient time to elaborate angiogenic factor and recovering the resulting angiogenic factor from the cells or cell product.

5 Claims, No Drawings

PRODUCTION OF ANGIOGENIC FACTOR BY CELL CULTURE

BACKGROUND OF THE INVENTION

This invention relates to the in vitro production of human angiogenic factor from the human diploid cell line IMR-90.

Angiogenesis, or the ability to stimulate blood vessel growth, is important to burn and wound healing and certain inflammatory reactions as well as to tumor growth. The substance that is released by tumors and provides vascularization has been named tumor angiogenesis factor (TAF) by Dr. Judah Folkman of the Harvard Medical School. *J. Exptl. Med.* 133, 275–88 (1971; *Ann. Surg.* 175, 409–16 (1972); *Cancer Res.* 34, 2109–13 (1974); and *Advan. Cancer Res.* 19, 331–58 (1974). Provision for the availability of TAF is particularly useful as an aid to the search for ways to inhibit neovascularization. While TAF also finds use in the development of tests such as an angiogenic assay or a diagnostic screening test for neoplasia, for use in patient treatment an angiogenic material derived from normal rather than tumor cells would be much preferred from the standpoint of safety.

Various investigators in the field have reported heretofore that angiogenic activity is either absent or weak in most normal tissue extracts or grafts or cell culture extracts. Thus, in a paper by Folkman on "Tumor Angiogenesis", *Advan. Cancer Res.* 19, 331–58 (1974), only two exceptions were found to the "general rule that normal adult and embryonic tissues do not induce neovascularization". The observed exceptions were that pieces of embryonic and adult mouse kidney induced mild neovascularization when grafted to the chorioallantoic membrane (CAM) of the chick embryo and that salivary gland from the adult mouse also seemed to be able to induce neovascularization on the CAM. In another paper from the same research group by Auerbach et al., *Int. J. Cancer* 15, 241–5 (1975), it was reported that control or irradiated placental and muscle tissue from rabbits did not cause a vascular response comparable to that obtained with Walker rat carcinosarcoma and other tumors either with or without irradiation. Klagsbrun et al., *Cancer Res.* 36, 110–14 (1976), subsequently reported that TAF was not detected in normal liver and kidney or in density-inhibited BALB/c primary mouse embryo or early passage human skin fibroblasts, but that density-inhibited BALB/c 3T3 and WI 38 human embryonic lung fibroblasts did produce TAF.

Another group of investigators, Wolf and Hubler, *Arch Dermatol* 111, 321–27 (1975), also investigated the elaboration of TAF by various implated tumors. In parallel tests, angiogenesis was found to be conspicuously absent after implantation of control materials and nevoid or normal cutaneous components with the exception of human and hamster epidermis.

Gimbrone and Gullino, *J. Nat. Cancer Inst.* 56 (2), 305–18 (1976), studied the implantation of mouse mammary tissue in rabbit cornea. They found that while neoplastic tissue stimulated blood vessel growth, normal tissue rarely produced any vascular change.

Phillips et al., *Int. J. Cancer* 17, 549–58 (1976) and 23, 82–88 (1979), found that rat liver, normal human kidney and various other normal or foetal tissues failed to induce angiogenesis.

On the other hand, significant angiogenic factor has been found in normal tissue by several investigators. Thus, Wolf et al., *J. Invest. Dermatol.* 61, 130–41 (1973), reported on an epidermal angiogenic factor from separated hamster epidermis and epidermal extracts as an exception to the general finding that normal tissues do not induce neovascularization when implanted onto the hamster cheek pouch.

Huseby et al., *Microvas. Res.* 10, 396–413 (1975), reported on a normal tissue explant system for 1-day old mouse testes that stimulated proliferation of host blood vessels in adult mice.

The corpus luteum was also found to produce a diffusible substance similar to TAF as a blood growth stimulant by Oehme et al., East German Pat. No. 128,368 (1977); and by Gospodarowicz et al., *Proc. Natl. Acad. Sci. USA* 75 (2), 847–851 (1978).

All of the foregoing normal human cells are derived from fresh tissue or primary cultures except the WI 38 cells. Fresh tissue and primary cultures are not, however, generally suitable sources of angiogenic factor except for limited research purposes or small scale production. In order to provide a commercially significant source of angiogenic factor in terms of ready availability and adequate supply, production by cell culture of a suitable cell line is deemed necessary. As a practical matter, the cell line should not only have specific angiogenic factor activity, but it should also have good cell growth characteristics in terms of rapid growth and production of angiogenic factor on a sustained basis.

The term "cell line" is used herein in conformance with the well-known art accepted definition published by Federoff in the *Tissue Culture Association Manual*, Vol. 1, No. 1, pp. 53–57 (1975).

Further background information on angiogenic activity in normal tissues can be had by reference to a review by Ausprunk in Chapter 10 of "Handbook of Inflammation", Volume 1, at pages 321 and 343–346, Series ed. Glynn et al, Elsevier/North Holland Biomedical Press, 1979.

DESCRIPTION OF THE INVENTION

The inventors have investigated numerous normal human cell lines for the production of angiogenic factor by cell culture but most of them have been eliminated as unsuitable candidates in view of their relatively poor angiogenic activity production or poor growth characteristics as above-defined.

A cell line that has now unexpectedly been found by the inventors to have good growth characteristics in cell culture and to be able to elaborate the desired angiogenic factor in suitable quantities is the human diploid cell line IMR-90. This cell line was derived from lung tissue of a normal human female fetus and was obtained at passage 7 in an unrestricted culture from the American Type Culture Collection, Rockville, Md., under the code designation ATCC CCL 186. It is also available from the Human Genetic Mutant Cell Repository of the Institute for Medical Research, Camden, N.J., as IMR-90. The initiation and characterization of this cell line is described in detail by Nichols et al., *Science* 196. 60–63 (1977). This cell line was reported to be developed as a replacement for the WI 38 cell line in support of research programs of the National Institute on Aging, general cell biology and related activities.

The cell line IMR-90 has not heretofore been known or proposed as a suitable source of angiogenic factor. Since it was known that angiogenic activity is absent or weak in most normal tissues, the suitability of cell line IMR-90 for production of angiogenic factor in accordance with this invention was an unobvious finding by the inventors. Moreover, another cell line which also was derived from fetal lung tissue and developed as a replacement for WI 38, namely MRC- 5 (available under ATCC CCL 171), was found by the present inventors to be a poor source of angiogenic factor relative to IMR-90.

The IMR-90 cell line was initially maintained at 37° C. as a monolayer in a series of 75 cm$^2$ T-flasks (Falcon Plastics) containing 50 ml Dulbecco's modification of Eagle's minimum essential medium (MEM) supplemented with 4.5 mg/ml glucose and 20% fetal bovine serum (KC Biologicals), without addition of any antibiotics. The flasks were charged with fresh medium every 1-2 days until confluency was reached in about 6-8 days.

It will be appreciated that other nutrient culture media for culture of the IMR-90 cells can be used in place of Dulbecco's MEM, for example, any of the well-known tissue culture media described by H. J. Morton, *In Vitro* 6, 89-108 (1970). These conventional culture media contain known essential amino acids, mineral salts, vitamins and carbohydrates. They are also frequently fortified with mammalian sera such as fetal bovine serum. Suitable growth of the cells can be carried out at about 35°-38° C., but cell proliferation is best at 37° C. Growth under these cell conditions for about 4-8 days generally is sufficient to produce the desired angiogenic factor.

Currently, four different bioassays are used to detect the presence of angiogenic factor. They are:

(1) The chorioallantoic membrane (CAM) of the 10 to 11 day-old chick embryo; Auerbach et al., *Devel. Biol.* 41, 391-94 (1974); Folkman, *Cancer Res.* 34, 2109-13 and 36, 110-114 (1976).

(2) The rat dorsal subcutaneous pouch; Folkman, *New Engl. J. Med.* 285, 1182-86 (1971); Phillips et al., *Int. J. Cancer* 17, 549-58 (1976).

(3) The rabbit cornea; Gimbrone et al., *J. Nat. Cancer Inst.* 50, 219-28 (1973); 52, 413-27 (1974).

(4) The hamster cheek pouch; Wolf et al., *J. Invest. Dermatol* 61, 130-41 (1973).

The CAM assay was used herein for convenience in that many duplicate samples can be tested inexpensively. According to this test method, the CAM is exposed through a window in the shell of a 9-day-old chick egg. On day 11, the sample is implanted and read at 48-72 hours. Active material induces new vessels to grow in toward the implantation site, thereby producing a spoke wheel appearance. The reaction can be graded qualitatively and capillary proliferation continues up to day 17.

In addition to growth in T-flasks, IMR-90 cells can also be grown in conventional roller bottles. By this technique, cylindrical bottles are inoculated with cells and supplied with suitable nutrient medium and then rotated slowly about the long axis of the bottles by rollers or wheels on which they lie. The cells adhere evenly over the glass surface and eventually spread to form a monolayer covering it. They can be removed by scraping or by treatment with trypsin until the cells become loose. Roller tubes as described in U.S. Pat. No. 3,450,598, are similarly useful for practice of the present invention.

Alternatively, the cells can be grown to confluency on synthetic beads, microcarriers and other such support surfaces supplying a high surface area, for example, glass beads or rods, silica spherules, microspheres of organic polymeric materials such as DEAE-Sephadex, polyacrylonitrile, polyacrylamide, polystyrene latex particles, and on elongated hollow or solid fibers, and other such support surface means.

Other suitable, large-scale equipment and procedures for growing cells on attached solid support which can be adapted for culture of the IMR-90 cell line will be readily apparent to the person skilled in the art by reference to well-known texts on cell culture and references cited therein such as, for example, Paul, "Cell and Tissue Culture", The Williams and Wilkins Company, Baltimore, Md., 4th ed. 1973, at pages 277-91; Kruse and Patterson, 37 Tissue Culture Methods and Apparatus", Academic Press, New York, 1973, at pages 283-392.

Various means can be used to recover fractions and concentrates of angiogenic factor from the cells and from cell product in the expended media following suitable growth of the cells. For example, the cells can be harvested and lysed by conventional means and angiogenic factor can then be recovered from the lysate by conventional techniques for the separation, isolation and purification of proteinaceous and other biological products in general. Suitable such procedures include, for example, dialysis, salt and solvent precipitation, ultracentrifugation, adsorption with gels, ion exchange chromatography with materials such as CM-cellulose, DEAE-cellulose, CM-Sephadex® and DEAE-Sephadex (Pharmacia AB) ion exchange resins, affinity chromatography, Sephadex gel filtration, electrophoresis such as agarose and polyacrylamide electrophoresis, SDS electrophoresis, isoelectric focusing and lyophilization. It will be appreciated that the inventors are not bound by any particular separation or isolation procedure or purity of the angiogenesis factor.

The following examples will further illustrate the invention although it shall be understood that the invention is not limited to these specific examples.

EXAMPLE 1

A sample of the IMR-90 (CCL 186) cell line was obtained from the American Type Culture Collection, Rockville, Md., at passage 7. The cell line was maintained at 37° C. as a monolayer in a series of T-75 cm$^2$ tissue culture flasks (Falcon Plastics) containing 50 ml. Dulbecco's MEM supplemented with 4.5 mg/ml glucose and 20% fetal bovine serum (KC Biologicals) without addition of any antibiotics. The flasks were charged with fresh medium every 1-2 days. When confluency was reached after 6-8 days, the cells were subcultured 1:3 in the following manner:

The spent medium was poured off the monolayer and discarded. The monolayer then was rinsed twice with 10 ml phosphate buffered saline (PBS) with 0.02% ethylenediamine tetra acetic acid (EDTA), at pH 7.4.

The PBS was prepared by dissolving 80 grams NaCl, 2 grams KCl, 2 grams $KH_2PO_4$ and 21.6 grams $Na_2HPO_4.7H_2O$ in 10 liters distilled water. The cells were released from the surface of the flask by adding 5 ml. 0.05% trypsin in PBS with 0.02% EDTA and allowing the thus treated cells to stand 5 minutes at room temperature (ca. 22°-25° C.). The suspension was divided equally into 3 fresh T-flasks containing 50 ml medium each.

CAM assays were carried out for obtaining an estimate of the angiogenic factor activity on the cell product after the cells had been thus subcultured through 15 passages. In general, 6 to 10 eggs were used per assay and 200 μg (dry weight) of lyophilized sample material was dissolved and redried onto a small plastic disk. The disk was placed sample side down onto the exposed CAM. The eggs were read for capillary proliferation toward the implantation site after 1 to 5 days following implantation and scored as active (positive, +) or inactive (negative, −), or as indefinite (neither positive or negative, ±) relative to known control results. A known positive sample of tumor angiogenic factor (from Walker 256 Carcinosarcoma cells) was usually run as a positive control while, for comparison, sterile filtered bovine serum albumin was always negative. The results of the assay were expressed as the number of positive eggs per total readable eggs. Eggs that were unreadable for various reasons, e.g. died during the assay, or were ±, were omitted from the assay results stated below.

In this example, nine 75 cm$^2$ T-flasks of confluent IMR-90 cells at passage 15 were each rinsed twice with 10 ml. PBS without EDTA and then incubated at 37° C. for 30 minutes in 5 ml each sterile distilled water. After mechanical disruption of the cells, the lysate was clarified by centrifugation (one 5-minute period at 5000×g, and then the supernatant for 30 minutes at 5000×g). The clarified lysate was evaporated on plastic disks and tested for angiogenic factor activity in the CAM assay with the following results:

| Concentrated lysate | 3 positive out of 8 eggs |
|---|---|
| Control sample from Walker 256 carcinosarcoma cells | 4 positive out of 5 eggs |

EXAMPLE 2

In this example, IMR-90 cells grown to confluency in T-flasks as in Example 1 were then subcultured in roller bottles through 13 passages. To inoculate a roller bottle, three T-flasks were washed with PBS with EDTA and then trypsinized as in Example 1. Two-thirds of the suspension from three T-flasks were added to a CO$_2$ gassed roller bottle containing 100 ml medium as in Example 1. The remainder of the suspension was added to three fresh T-flasks. Confluent roller bottles were split 1:3 by the same procedure as the T-flasks in Example 1, except that 25–30 ml PBS with EDTA were used for each rinse and 10 ml of the trypsin solution was used to suspend the cells. Roller bottles were incubated 5 minutes at 37° C. on a roller deck during the enzyme treatment.

After 18 roller bottles at passage 13 had been grown to confluency (750 cm$^2$ available surface/bottle), each bottle was washed twice with 25 ml PBS without EDTA. Twenty-five ml. of sterile water was then added to each bottle, and the cells were incubated for 30 minutes at 37° C. The cells were then lysed by mechanical disruption. The lysate plus a 25 ml water rinse of each bottle was stored at −20° C. for further use or fractionation.

A portion of the above stored lysate was fractionated as follows: The lysate was unfrozen and clarified by centrifugation (one 5-minute period at 5000×g, and the supernatant again at 5000×g for 30 minutes). The clarified lysate was concentrated to about 200 ml and dialyzed into low salt phosphate buffer (0.1 M NaH$_2$PO$_4$, 0.02% NaN$_3$, pH 6.1) in a Millipore Pellicon ® cassette concentration system. The concentrated lysate was added to 1.5 grams of carboxy-methyl (CM) Sephadex (particle size 40–120 μ, Sigma Chemical Co., catalog #C-50-120) which had been previously swollen in low salt phosphate buffer. After stirring for 30 minutes at room temperature, the mixture was filtered and the filtrate was retained as the CM-I fraction. The CM-Sephadex gel was rinsed with low salt phosphate buffer and then poured into a glass column (2cm. diameter). A high salt phosphate buffer (1 M NaCl, 0.1 M NaH$_2$PO$_4$, 0.02% NaN$_3$, pH 6.1) was applied to the column to release the protein from the CM-Sephadex. The column was set up so that the eluate flowed through a LKB Unicord II monitor (LBK Instruments, Inc.) set at 280 nm which recorded any protein eluted from the gel. The eluate was collected in fractions, with retention of that fraction (CM-II) which corresponded to the protein peak on the monitor.

Both the foregoing CM-I (35.3 mg. protein) and CM-II (1.9 mg. protein) fractions were dialyzed against distilled water and lyophilized. The lyophilized fractions were tested for angiogenic factor in CAM assay as in Example 1 with the following results:

| CM-I | 6 positive out of 6 eggs |
|---|---|
| CM-II | 4 positive out of 5 eggs |
| Control Sample from Walker 256 Carcinosarcoma cells | 4 positive out of 5 eggs |

EXAMPLE 3

Twenty-six roller bottles of IMR-90 cells at passage 16 were grown to confluency and harvested as described in Example 2. Both CM-I (74 mg. protein) and CM-II (2.8 mg. protein) were isolated as above and tested for angiogenic activity in the CAM assay with the following results:

| CM-I | 3 positive out of 5 eggs |
|---|---|
| CM-II | 3 positive out of 5 eggs |
| Control sample from Walker 256 Carcinosarcoma cells | 5 positive out of 7 eggs |

EXAMPLE 4

Two hundred and sixty-seven roller bottles at passages 12 through 18 were grown to confluency and harvested as described in Example 2. Both CM-I (1.1 grams protein) and CM-II (70 mg. protein) were isolated. An aliquot of CM-II lyophilized material was dissolved in PBS without EDTA and run through a Sephadex G-10 (Sigma Catalog #G-10-120) column with distilled water. The excluded front material was lyophilized and tested for angiogenic factor activity in the CAM assay with the following results:

| CM-II | 4 positive out of 5 eggs (100 μg/disc) |
|---|---|
| Control Sample from Walker 256 Carcinosarcoma | 5 positive out of 7 eggs (200 μg/disc) |

The CM-Sephadex used in the foregoing examples is a well-known cross-linked dextran material having carboxy-methyl functional groups and serves as a weakly acidic cation exchanger. Its use for obtaining an active fraction of tumor angiogenic factor from tumor cells is described by Tuan et al., *Biochemistry* 12 (17), 3159–65 (1973).

Various other examples of the invention will be apparent to the person skilled in the art after reading the present disclosure without departing from the spirit and scope of the invention. It is intended that all such other examples be included within the scope of the invention.

What is claimed is:

1. Process for the production of human angiogenic factor in vitro comprising growing the human diploid cell line IMR-90 on support surface in nutrient culture medium at about 35°–38° C. for a sufficient time to elaborate angiogenic factor and isolating the resulting angiogenic factor from the cells or cell product.

2. The process of claim 1 in which the nutrient culture medium is Dulbecco's modification of Eagle's minimum essential medium.

3. The process of claim 1 in which the nutrient culture medium is fortified with mammalian serum.

4. The process of claim 1 in which the angiogenic factor is isolated by extraction from the cells.

5. The process of claim 1 in which the nutrient culture medium is Dulbecco's modification of Eagle's minimum essential medium and is fortified with fetal bovine serum and in which the angiogenic factor is isolated by extraction from the cells and concentration by carboxymethyl Sephadex chromatography.

* * * * *